(12) United States Patent
Caplygin

(10) Patent No.: US 7,211,050 B1
(45) Date of Patent: May 1, 2007

(54) SYSTEM FOR ENHANCEMENT OF NEUROPHYSIOLOGICAL PROCESSES

(76) Inventor: Dimitri Caplygin, 1009 Rose Bank Way, Hope Island Resort, Queensland 4212 (AU)

( * ) Notice: Subject to any disclaimer, the term of this patent is extended or adjusted under 35 U.S.C. 154(b) by 639 days.

(21) Appl. No.: 10/018,733

(22) PCT Filed: Jun. 15, 2000

(86) PCT No.: PCT/AU00/00661

§ 371 (c)(1),
(2), (4) Date: Mar. 11, 2003

(87) PCT Pub. No.: WO00/77760

PCT Pub. Date: Dec. 21, 2000

(30) Foreign Application Priority Data

Jun. 15, 1999 (AU) .................................... PQ0933
Aug. 13, 1999 (AU) .................................... PQ2183

(51) Int. Cl.
*A61B 5/04* (2006.01)
*A61B 13/00* (2006.01)
*A61B 3/02* (2006.01)

(52) U.S. Cl. ...................... 600/558; 600/544; 600/545; 351/222

(58) Field of Classification Search ................ 600/300, 600/301, 558, 26, 27, 544, 546, 545; 351/222, 351/237, 238, 239
See application file for complete search history.

(56) References Cited

U.S. PATENT DOCUMENTS

| | | | | |
|---|---|---|---|---|
| 4,474,186 A | 10/1984 | Ledley et al. | | |
| 5,344,324 A | * 9/1994 | O'Donnell et al. | ......... | 434/258 |
| 5,363,154 A | 11/1994 | Galanter et al. | | |
| 5,377,100 A | 12/1994 | Pope et al. | | |
| 5,565,949 A | * 10/1996 | Kasha, Jr. | .................... | 351/224 |
| 5,737,060 A | * 4/1998 | Kasha, Jr. | .................... | 351/224 |
| 5,852,489 A | 12/1998 | Chen | | |
| 5,920,374 A | 7/1999 | Vaphiades et al. | | |
| 5,953,102 A | * 9/1999 | Berry | ......................... | 351/247 |
| 6,213,956 B1 | * 4/2001 | Lawton | ...................... | 600/558 |
| 6,364,845 B1 | * 4/2002 | Duffy et al. | ................ | 600/558 |

FOREIGN PATENT DOCUMENTS

| | | |
|---|---|---|
| CA | 2012863 A1 | 9/1991 |
| WO | WO 95/29447 A1 | 11/1995 |
| WO | WO 98/44848 A1 | 10/1998 |

OTHER PUBLICATIONS

PCT International Search Report; PCT/AU00/00661 (WO 00/77760); International Filing Date Jun. 15, 2000; Applicant: Dimitri Caplygin.

* cited by examiner

*Primary Examiner*—Max F. Hindenburg
*Assistant Examiner*—Jonathan Foreman
(74) *Attorney, Agent, or Firm*—Lerner, David, Littenberg, Krumholz & Mentlik, LLP

(57) ABSTRACT

Treatment apparatus and method for the enhancement of neurophysiological processes of a patient's visual system utilizes a computer generated display that provides a patient simultaneously with passive visual stimulation images and visual cognitive exercises. The stimulation images include moving elements having edges or points of contrast. The exercises include visual and phonological elements. The invention is used to treat reading, writing and speech disorders, and attention deficit hyperactivity disorder, as well as having broader applications for example in sports sciences.

22 Claims, 17 Drawing Sheets

Audio: "Benjamin is a happy boy"
"Harold is unhappy"
"Match the name with the face by dragging a name over to the face"
Fig. 16

SYSTEM FOR ENHANCEMENT OF NEUROPHYSIOLOGICAL PROCESSES

BACKGROUND OF THE INVENTION

This invention relates to a system for the enhancement of the neurophysiological processes of a person, in particular those processes associated with reading, writing and speech. The invention was conceived in the context of treating reading, writing and speech disorders but has far broader applications including the treatment of Attention Deficit Hyperactivity Disorder (ADHD) and the enhancement of a person's perception of movement required for example, by sportspeople or defence force personnel.

Since the late nineteenth century it has become increasingly noticeable that a substantial percentage of the population possess no abnormalities in conventional vision, hearing or intelligence, yet display debilitating disorders of reading, writing and speech.

Although there is a connection between these different types of disorders, reading disorders have attracted the most concern and attention and are thought to afflict up to 15% of the world's population. Reading disorders are psychologically and economically damaging to a person, are largely hereditary and have been considered to be incurable.

A growing body of neuroscientific research has linked many of such disorders with neural debilitation's in different areas of the brain.

Several groups of scientists utilising modern non-invasive diagnostic techniques such as functional Magnetic Resonance Imaging (fMRI) or Positron Emission Tomography (PET) have found significant differences in brain activity, in particular in areas of the brain associated with the perception of movement, between those with reading disorders and those without.

The perception of sight begins when visible light contacts the retina at the back of the eye. Photoreceptor cells known as rods and cones are stimulated by this light to produce electrical impulses. These impulses travel from the retinal ganglion cells via their axons and ultimately connect with the visual centres of the brain, in particular the visual cortex. The connection between the retina and the visual cortex includes a small midbrain nodule called the lateral geniculate body. This body is divided into two layers, one of which is part of the magnocellular pathway and the other a part of the parvocellular pathway. The divided signal from these visual pathways continues to the visual cortex and the extrastriate visual cortex at the back of the brain to undergo a multiplicity of complex processes to emerge as a perception of sight.

The magnocellular and parvocelluar systems are part of the retino-geniculo-cortical pathway system. The magnocellular pathway has evolved to be able to process rapid movements of low contrast images in conditions of low luminance but with relatively poor colour sensitivity, whereas the parvocellular pathway processes fine stationary detail in conditions of brightness and with greater colour sensitivity.

Research has shown that both pathways are parallel processing systems involved in developing and sustaining an acute kind of depth perception called stereopsis. The magnocellular system is responsible for motion stereopsis, which is vital for normal reading. The parvocellular system is responsible for static stereopsis. Deficiencies in either pathway can affect stereopsis which can lead to an inability of a person to property process visual images.

Furthermore, it has been suggested in some research that the debilitation of receptive cell fields in the magnocellular pathway causes this parallel processing system to deliver mistimed visual information to the visual cortex. This, it has been hypothesised, causes instability of viewed text in some patients resulting in their reading disabilities.

The visual system is predominantly edge seeking and motion biased in character. Holding a steady fixation on a visual target is indeed not possible. When a steady fixation is induced in a laboratory, the visual image fades.

Oculographic recordings have demonstrated three types of eye movements that occur during fixation: microsaccades, (small, high-speed adjustments of fixation), fixation drift and high frequency tremors.

Saccades used in normal vision bring items of visual interest into the foveal area of the retina for examination under conditions of maximum acuity. Microsaccades are similar to saccades, except that the amplitudes are smaller.

Microsaccades occur about 2 to 3 times per second, along with a slow fixation drift, which in combination prevent fading of the retinal image. The manner in which microsaccades and fixation drifts are interposed is dependent upon an individual's optokinetic control. Such control is in turn influenced by neurophysiological debilitations that are partially non-visual in source.

Oculographic recordings have shown that during reading a stereotyped "staircase" pattern of eye movements occurs, consisting of alternating saccades and periods of fixation. During the pauses, semantic identification and recognition of characters is thought to occur. Each saccade moves the fovea (the portion of vision with the greatest acuity), about eight characters to the right. At the end of a line, a large saccade to the beginning of the next line occurs and the behaviour is repeated.

An optokinetic deficit could lead to reading disorders if it prevents microsaccades from occurring at the required speed and endurance, and if it prevents fixation drift to be controlled with enough endurance. If this deficit is compounded by some language or phonological impairment, then semantic recognition, an essential link in the reading chain, can be even more difficult to achieve.

During more rapid normal reading or the normal viewing of more complex visual images, the eyes employ a healthy motion and static stereopsis (depth perception) to find visual 'cues'. They pause at very small time intervals and look directly at what the brain considers are the more important visual elements and deduces what is in between.

It has been suggested that some normal readers employ a strategy that uses "habitually preferred" patterns stored in their memory. This involves an initial visual scanning phase described as to "look without seeing" in which an internal model is formed in order to then "see without looking". Finally, there is a rapid model verification phase to "look and see". This requires rapid saccades to move the high acuity area of the fovea to the salient features for verification.

An ability to provide the required saccades, control of fixation drift, recognition of semantics, stereopsis and an adequate visual working memory, are essential prerequisites for good reading.

Furthermore, because of the relationship within the brain of the magnocellular and parvocellular pathways with other neurophysiological processes such as speech, hearing and kinaesthetic and somatosensory processes, an inability to properly process visual images can lead to disorders in these other processes.

From the large numbers of reading disorder treatment providers, few have attempted to search for curative solutions, particularly based on visual causes, in the belief that cures are not possible. Indeed most reading disorder associations and much of the scientific community still support this view.

The beginnings of a visual based curative approach commenced with the development of a simple apparatus called the CAM visual stimulator, developed in Cambridge England in the mid 1970s. The CAM stimulator was developed not for the treatment of reading disorders, but for the orthoptic treatment of pathologic binocularity, a condition where fixation errors of the eyes cause the brain to favour signals from a dominant eye and tends to suppress signals from the weaker eye. The stimulator comprised rotating paper discs covered with painted gratings intended for visual stimulation. This apparatus gained wide interest and exposure for the orthoptic treatment of ocular fixation disorders but with limited success.

Another version of the CAM apparatus was developed in Australia in the late 1970s, and comprised similar rotating discs with painted gratings, but with the addition of a diffuse light source from between the gratings. This second version of the CAM apparatus was the subject of Australian patent application no. 70697/81 by A. M. Lawson. It was also conceived and originally used for the same treatment of pathologic binocularity, although later was used for treatment of visual dyslexia.

Whilst these prior art apparatus achieved some success in treating the fixation disorders for which they were designed, their success in treating reading disorders was limited due to the complex nature of the retino-genicular-cortical pathways and the very limited range of stimulations that the rotating discs could provide. The edges of the stripes that provided the visual cues to the patient had a constant locus of movement, that being a circular path, and only provided the correct stimulation to a limited number of cells in the visual cortex and for a brief period of time as the edge passed through a particular orientation. The only variation in the stimulation was achieved by changing the disc to one with a different spacing and width of stripes. This variation could not be achieved without disruption to the patient's treatment.

The present invention seeks to provide apparatus and method wherein a patient can receive a more complete set of stimulations than was possible with the prior art.

SUMMARY OF THE INVENTION

In a first aspect, the invention resides in apparatus for the enhancement of neurophysiological processes of a patient including first visual display means for viewing by said patient and computer processing means producing an output to said visual display means to cause a display on said display means, said display including computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise.

The invention also resides in a method of enhancing neurophysiological processes of a patient by the stimulation of receptive cell fields in the visual pathways of the patient between the retina and the visual cortex, the method including the steps of generating an output from computer processing means to cause a display on visual display means for viewing by said patient, said display including at least one visual cognitive exertion exercise and at least one visual stimulation image including one or more therapeutic display elements targeted to stimulate selected ones of said receptive cell fields, said therapeutic display elements including one or more moving contrast edges, wherein said visual stimulation image provides therapeutic stimulation to selected ones of said receptive cell fields whilst said patient is performing said visual cognitive exertion exercise.

The present invention can provide many benefits to a patient not possible with the prior art treatment systems including a visual stimulation image that can be varied to provide the stimulation required by the patient and in particular can be varied without a discontinuity in the patient's treatment. Furthermore the visual display elements can be generated as direct light objects which are far more effective in stimulating the cell fields of the retino-geniculo-cortical pathway system than the diffuse light sources from between the rotating striated discs of prior art.

In a further embodiment the invention resides in apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise and wherein said apparatus includes means for varying at least one, and preferably at least two of spatial density, luminance, contrast, colour, shape, velocity, orientation, direction of motion and locus of movement of said plurality of therapeutic display elements.

In a further embodiment, the invention resides in apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more contrast edges moving in a substantially linear path, wherein said therapeutic display elements are displayed on said visual display means so as to provide therapeutic stimulation to said receptive cell fields of a patient whilst said patient is performing said cognitive exertion exercise.

In a still further embodiment, the invention resides in apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise, said apparatus further including means for generating an auditory cognitive exertion exercise including one or more auditory signals related to at least one of said visual cognitive exertion exercises.

In yet a further embodiment, the invention resides in apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means and patient input means, said display including successively displayed patient interactive visual cognitive exertion exercises and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercises wherein said therapeutic stimulation elements are displayed on said visual display means so as to provide therapeutic stimulation to said receptive cell fields of a patient whilst said patient is performing a displayed cognitive exertion exercise and wherein a next cognitive exertion exercise is displayed in response to input from said patient.

The therapeutic display elements may be anything capable of not only stimulating the receptive cells fields along the neurophysiological pathways of a patient but also providing enhancement of the neurophysiological processes associated with that stimulation.

A particular advantage of the present invention is that it provides the means to vary the visual stimulation image(s) whilst the patient is performing a cognitive exertion exercise. This ensures that as many of the receptive cell fields of the patient as are necessary or possible receive adequate stimulation. The changes to the visual stimulation image can be made abruptly by displaying a fresh image or can be made to occur by graded changes so that a dynamic, constantly evolving visual stimulation image is displayed. The changes can all occur without disrupting a patient's focus on the cognitive exertion exercise the patient is performing. The variations that can be made include changes in the colour, shape, contrast, luminance, spatial density, velocity or locus of movement of the moving visual display elements.

In a preferred embodiment, the invention further includes means for providing a different visual stimulation image to each eye of a patient and/or means for occluding one of a patient's eyes from the display. In this embodiment, the level of occlusion may be varied.

In a further preferred embodiment, the invention includes a second visual display means to be viewed by a therapist and therapist input means allowing a therapist to provide inputs to the computer processing means to vary the display.

In yet another embodiment, the invention includes feedback means providing feedback of a patient's performance to the computer processing means and preferably includes means for altering the display in response to said feedback in order to optimise a patient's performance.

The invention will now be described by way of example only and with reference to the accompanying figures as described below

BRIEF DESCRIPTION OF THE DRAWINGS

FIG. 16 is a second auditory cognitive exertion exercise.

DETAILED DESCRIPTION OF PREFERRED EMBODIMENTS

Figure 1:
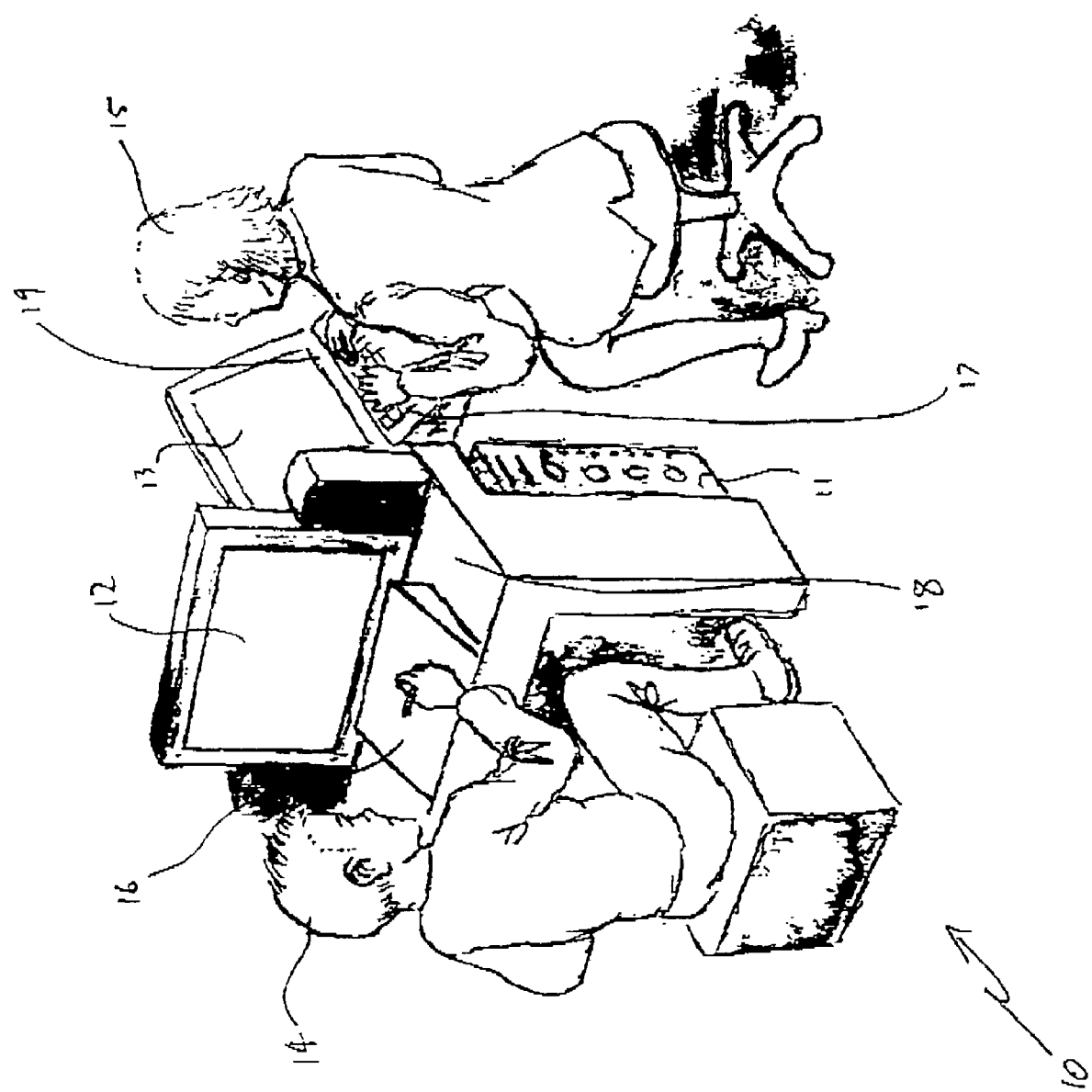
FIG. 1 is an illustration of the apparatus of the present invention.

With reference to FIG. 1, apparatus according to the invention is shown generally at 10 and includes a computer processor 11, a patient console 18 including a patient visual display unit (VDU) 12 and patient input means 16, and a therapist console 19 including a therapist visual display unit 13 and therapist input means 17. A patient 14 is shown at the patient console 18 whilst a therapist 15 is shown at the therapist console 19. The position of the patient console 18 is such that a patient 14 is unable to view the VDU 13 of the therapist console whilst viewing the patient VDU 12. In the case of the patient console shown, the patient input means is an electronic writing pad whilst the therapist inputs information via a conventional keyboard 17.

Figure 2:
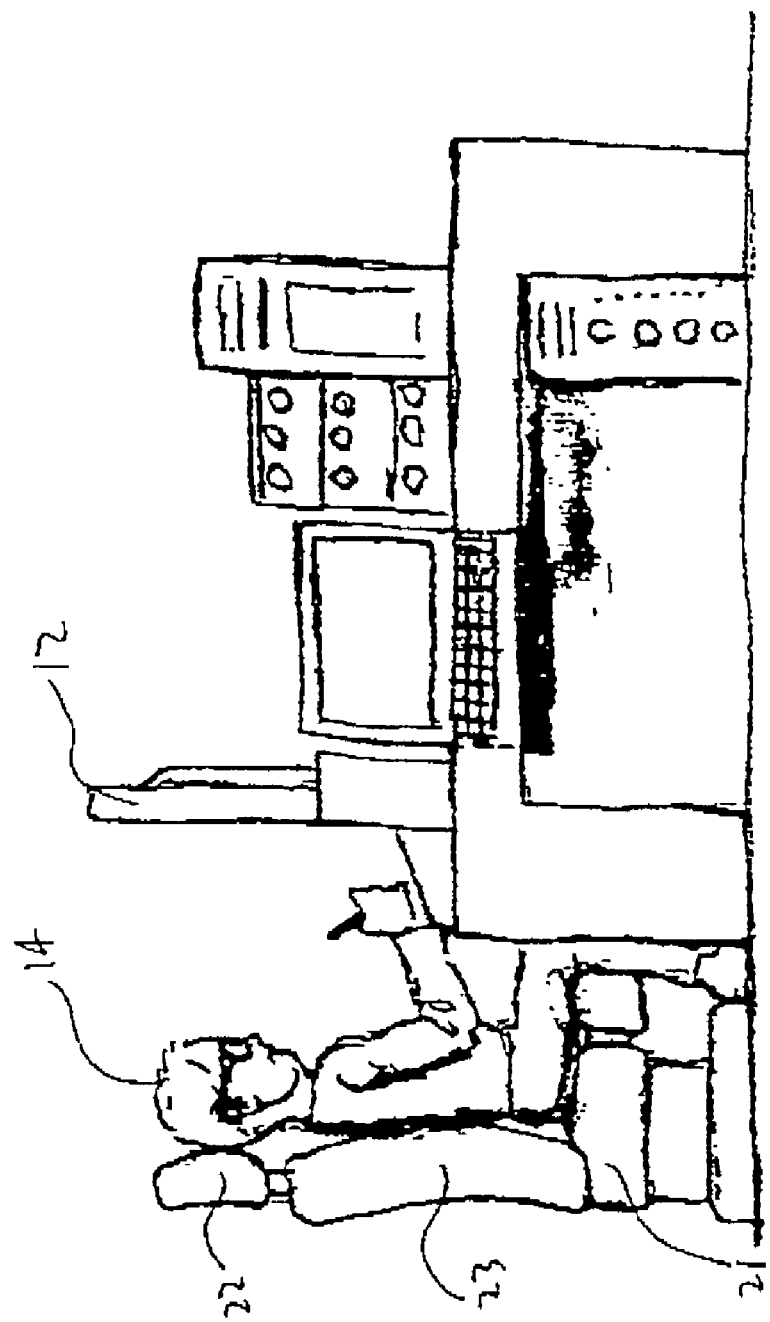
FIG. 2 shows a side view of apparatus according to the invention.

In FIG. 2 an alternative arrangement is shown wherein the patient 14 is seated on an electronically adjustable seat 21 that can be moved up and down as well as laterally. The headrest 22 and backrest 23 can also be controlled to ensure the location of the patient's eyes relative to the patient VDU 13. The seat controls, including the controls for the headrest and backrest form part of the therapist console 19. A patient's positional settings may be stored in the computer processor to provide consistency at subsequent treatment sessions.

The therapist 15 is presented with the same display as the patient and is able to control the parameters of the treatment. A comparison of how the patient has progressed and how the patient relates to those with similar disorders is also available for viewing by the therapist.

Figure 3:
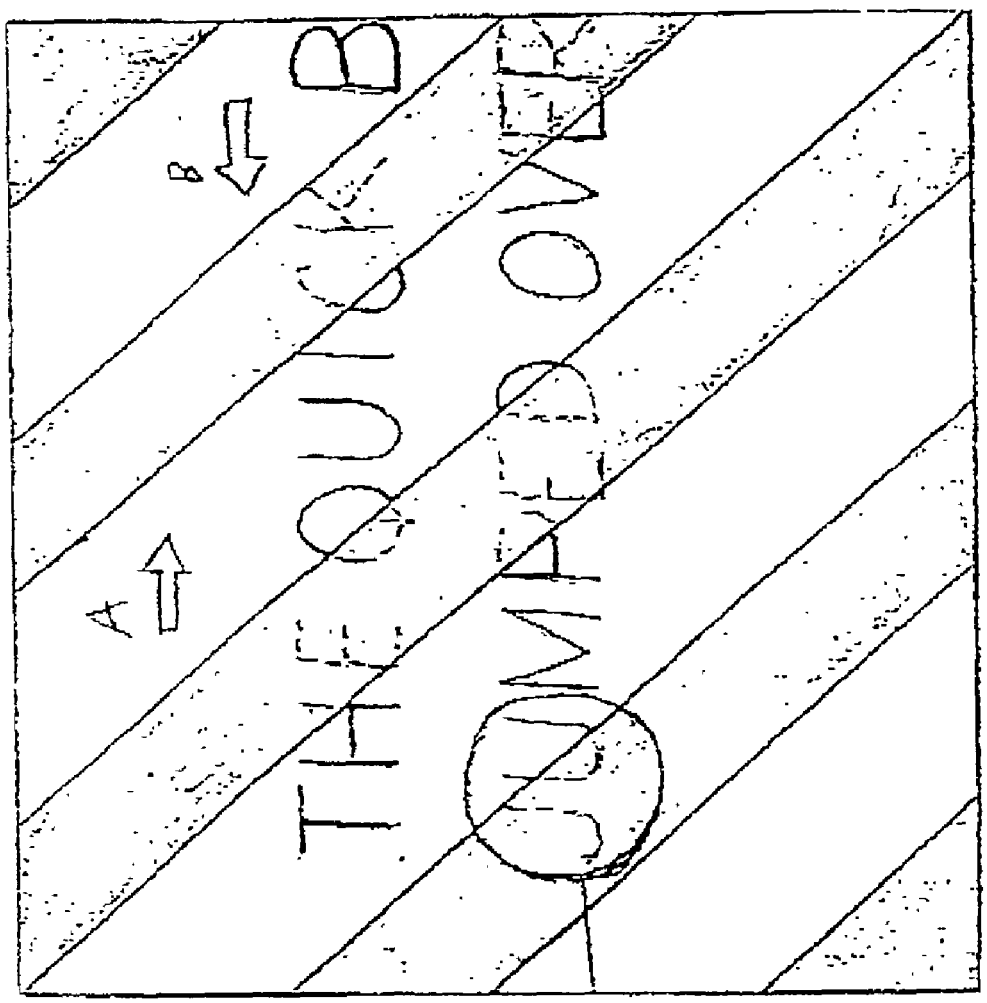
FIG. 3 shows a display of a visual cognitive exertion exercise and visual stimulation image.

An exemplary display to be provided on the patient VDU is shown in FIG. 3 and includes a plurality of inclined stripes moving in a linear path across the display unit in the direction of arrow A. Moving in the opposite direction as indicated by arrow B is a cognitive exertion exercise comprising words or phrases which a patient must remember and write down after they disappear, or select and form into a sentence. Thus the exertion exercise can improve or enhance other aspects of a patient's neurophysiological processes such as working memory whilst focussing the patient's attention onto the display to ensure they receive the visual stimulation from the moving elements.

Furthermore, the present invention allows a multitude of visual stimulation images to be presented to a patient without disruption to the patient's treatment and allows variations within those images to be made to maximise the benefit that a patient receives. For example in the above described display of FIG. 3 the stripe width and spacing can be adjusted by simple inputs from the therapist as can the colour, contrast, direction etc of the stripes. Non-cortical stimulation elements can also be added as described below. In this way a therapist can ensure that as many receptive cell fields as possible along the retino-genicular-cortical pathway are properly stimulated.

It is an objective of the present invention to stimulate as many receptive cell fields as is possible, that are involved in processing the type of vision that is required for reading and for the perception of movement.

The beginning of the retino-geniculo-cortical pathway is the retina, which contains a large number of different cell types, such as ganglion cells, horizontal cells, bipolar cells and amacrine cells. Within each type there are numerous subtypes. These are organized in a remarkable concentric configuration. Hence stimulation of these by light require spots and annuli of light. The response of these is highly variable, depending upon whether the centre spot is stimulated only, or the annulus, and whether the centre and annulus are stimulated simultaneously. Varying the width of the annulus also influences the response.

The excitation that the stimulation produces in these cells is also different according to cell type. For on-centre cells, the field centre is excited by light stimuli, whereas the surround is inhibited by light stimuli and excited by dark stimuli. For off centre cells the reverse is true.

From some tell types, excitation is either on or off, or tonic, and is sustained. For others it is transient, or phasic, meaning it is proportional to the stimulation.

The maximal response is obtained by choosing a spot size equal to the diameter of the receptive field centre. If the spot is larger, then the response is attenuated, indicating antagonism between the centre and the surround subfields.

Cells in the lateral geniculate body are similar to that of the retina but with differences in response. The surround of geniculate cells is relatively more effective at canceling the centre, making geniculate cells even less responsive to the illumination of the entire receptive field.

The parvocellular and magnocellular pathways from the retina remain segregate at the lateral geniculate body. Their respective cell fields have their particular stimulation requirements.

The most common type of parvo cell has a standard centre-surround receptive field arrangement, where the centre and the surround have different spectral sensitivities. A typical such cell might give an 'on' response to a red spot and an off response to a green annulus. A second type of parvo cell provides a response to coloured light wherever it is applied in the receptive cell field. A third type is similar to the second type except that the receptive cell field is indifferent to colour wherever it is applied.

The majority of magno cells are indifferent to colour and have centre-surround receptive fields, similar to the third type of parvo cell above. Another type of magno cell however, does have the unusual behaviour of responding with a dramatic, prolonged silence to a large red spot.

Figure 4:
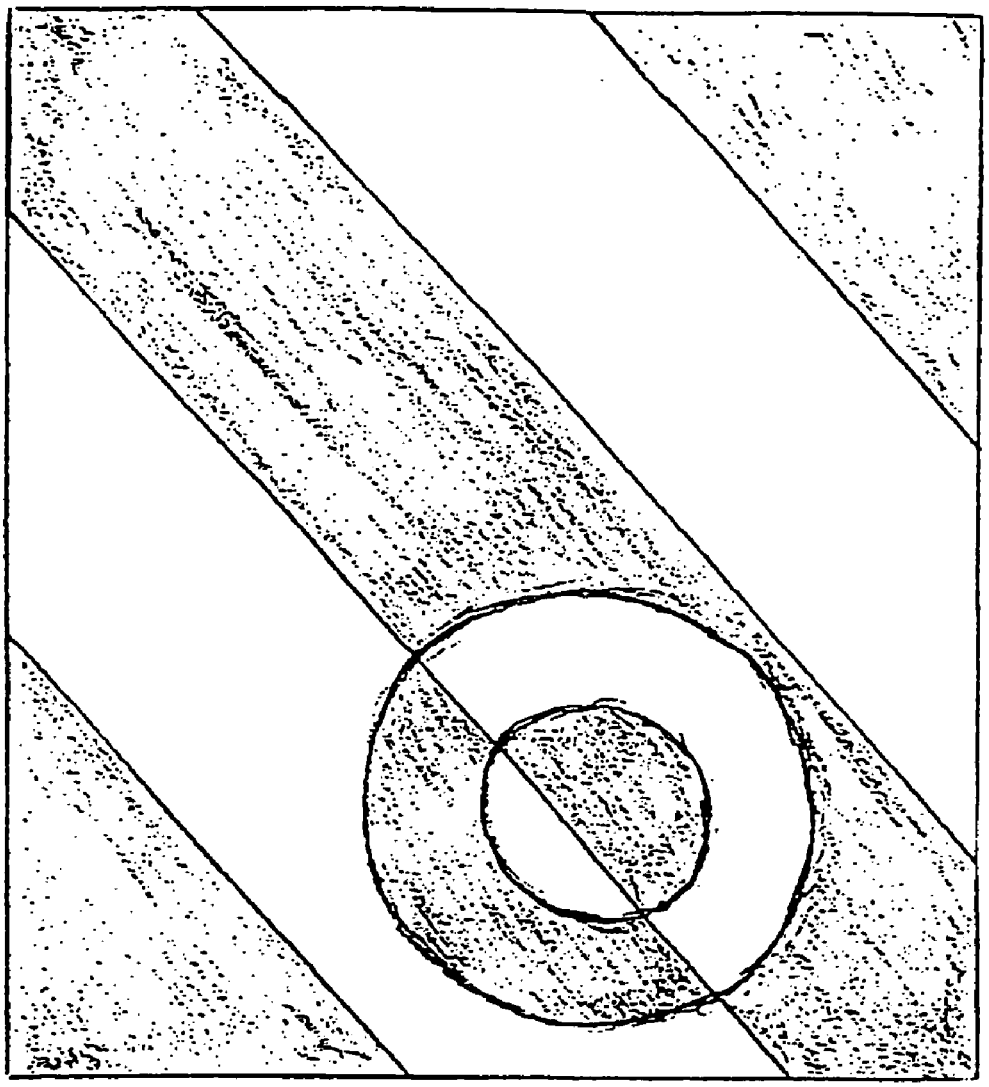
FIG. 4 is an example of predominantly non-conical stimulation elements.

A stimulation image as shown in FIG. 4 is appropriate for stimulation of the concentrically organised cell fields in the visual pathways before the visual cortex and in some cases beyond. The image consists of annuli and dots of different dimensions and colour combinations, designed to match the particular cell sizes and characteristics of these cell fields. The dots and annuli are shown in FIG. 4 together with a plurality of stripes that may form part of the cortical stimulation described below. At the interface where a stripe meets a boundary of the dot or annuli, a contrast change occurs. Relative movement between the dot and the stripe creates a dynamic stimulation as the size of a particular contrasting feature changes. It is preferred that at least some of the annuli/dots move randomly to provide contrast boundaries covering the full range of dimensions and directions. The centre dot is approximately 15 mm in diameter with a surrounding annulus of approximately 25 mm, though the dimensions may be varied to correspond and provide stimulation to different receptive cell fields.

The proper utilisation of this image requires particular management not to conflict with the cognition exertion exercise, particular where the exercise includes fragmented tasks where objects in the exercise are obstructed by the moving elements of the stimulation image. Hence a high degree of adjustability and choice is incorporated in this image.

There is an automatic contrasting feature that allows dots and annuli to pass through any opaque object and instantaneously switch contrasting so that there are always dark edges for the patient to look at.

There is a density selection feature, which enables several dot/annuli density combinations to be chosen, either uniformly across the view field of the monitor, or in random appearing clusters, or with a centre display view bias. This selection can be performed by a therapist in response to either passive or active feedback from the patient in order to maximise the stimulation to the patient, or to concentrate on specific receptive cell fields. Alternatively, computer software can be used to make progressive adjustments to the spot/annuli size and density to ensure that the full range of stimulations are provided.

Once an adjustment has been made, the computer software can ensure that every position in the view field has been occupied by a moving element comprising an annuli and a dot of particular dimension and colour combination, before the software automatically makes a progressive adjustment for the next size element.

The end of the retino-genicuar-cortical pathway is the visual cortex. The visual cortex has been divided into more than thirty functional areas that have so far been identified. The areas that process the incoming signal first have been designated as V1, V2, V3, V4 & V5.

V1 transfers visual information from the magnocellular and parvocellular systems to V2. This is consistent with research findings that V2 has a high proportion of both colour sensitive and motion sensitive receptive cell fields. Furthermore, the connection of both pathways also suggests that V2 plays a part in both motion and static stereopsis.

V1 also sends magnocellular visual information to V3, which contains mainly motion sensitive receptive field cells, but few if any, colour sensitive cells. It is therefore likely that V3 participates mainly in motion stereopsis.

V4 contains largely colour sensitive receptive cell fields which are used to process colour, after the visual information regarding colour has already been processed by V1 and V2.

V5 is referred to as the middle temporal area. The striking aspect about V5 is that almost all the receptive cell fields are sensitive to both direction and motion, as well as to eye movement. Some of these cells are indifferent to stimulus shape and are particularly sensitive to the direction of that motion. Hence there is a major magnocellular projection from V1 to V5.

There are therefore three separate but interconnected pathways through V1, V2, V3, V4 & V5. A first pathway sends mainly parvocellular visual information from V1 to V1 to V3. The second pathway takes mainly magnocellular visual information from V1 to V2 and then onto V5, while the third runs both magnocellular and parvocellular visual information from V1 to V2 and then to V4.

The cells of the visual cortex are different to those encountered at the retina or lateral geniculate body and are classified in terms of simple cells, complex cells, and their receptive field hierarchy.

Simple cells can be described by their response to a single spot and whether it is excitatory or inhibitory. They exhibit summation within their separate excitatory and inhibitory subfields and antagonism when both regions are stimulated simultaneously. In this respect, simple cells are similar to the centre surround cells of the lateral geniculate body. The critical distinction is that the geniculate cells are concentrically arranged, whereas the cortical cells are organised into parallel, flanking subfields, separated by straight boundaries.

The geometry of the subfields varies considerably among simple cells. However, for all simple cells, the best stationary stimulus is a slit or bar of light exactly the right dimensions to activate only an excitatory or on response, or an inhibitory or off response.

Correct orientation of the stimulating bar is crucial to obtain the maximum response. If the stimulating bar is not parallel to the axis of the receptive fields, it will stimulate part of the inhibitory subfield and fail to stimulate the entire excitatory subfield. Orientation selectivity is an essential feature of cortical simple cells. All orientations are represented equally in the visual cortex.

Simple cells respond briskly to moving bars, slits or edges and usually fire a burst of 'spikes' just as a moving light bar enters an excitatory region. The most vigorous discharge is provoked by simultaneously leaving an inhibitory zone and entering an excitatory zone. Cells with a symmetric subfield arrangements generally given an equal response to movement in either direction. Cells with asymmetric subfields often give unequal responses to movement in the opposite direction. The optimal speed of stimulus movement can also vary among simple cells.

Complex cells cannot be categorised with stationary stimuli into excitatory and inhibitory sub regions. They give inconsistent on-off responses when tested with stationary slits or spots of light. However, when a light slit is swept across the receptive field, it elicits a sustained barrage of impulses. A complex cell may respond to movement of the light stimulus anywhere within the receptive field, provided the stimulus is oriented correctly.

Ordinary complex cells show summation by responding more robustly as the length of a light stimulus is increased. The maximum response occurs when a slit or bar equals the full length of the cell's receptive field. Extending the stimulus beyond the length of the receptive field augments the response no further.

Receptive cell fields in V5 respond well to a light spot, bar, or slit moved briskly in a preferred direction, and give no response to an opposite direction. For these cells, the stimulus shape matters little as long as the direction of the movement was correct. Other cells in V5 required a properly orientated slit or bar moved in a certain direction. The receptive cells in V5 resembled those in V1 except those in V5 where much larger and are direction selective.

A simple linear omni-directional image for stimulating receptive cell fields in the visual cortex is described with reference to FIG. 5. This figure shows a plurality of parallel inclined stripes approximately 15 mm wide that move in a linear path in a direction transverse to the longitudinal direction of the stripes as indicated by arrow A. The stripes move in their path with a sinusoidal velocity with an average speed of approximately 75 mm per second. A background rotation as indicated by arrow B is imposed to change the locus of movement of the stripes and ensure that all orientations of the edges are displayed to the patient. The rotation is effected stepwise by rotating the plant of stripes 2° every 5 seconds. Once the plane of stripes has been rotated through 180° so that all orientations have been displayed, the stripe width and spacing is adjusted, preferably in increments of approximately 0.5 mm, and the rotation repeated.

Figure 5:
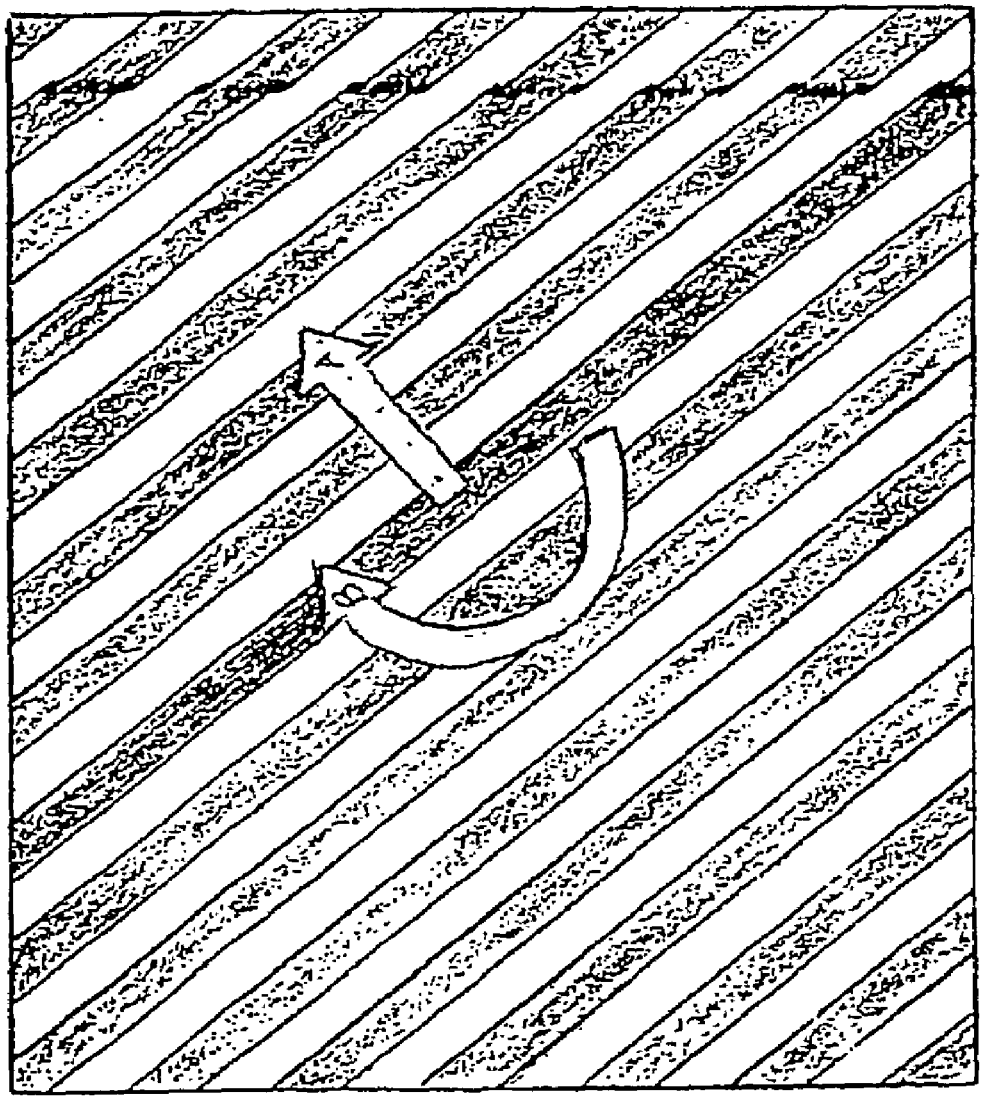
FIG. 5 is an example of predominantly cortical stimulation elements.
Figure 6:
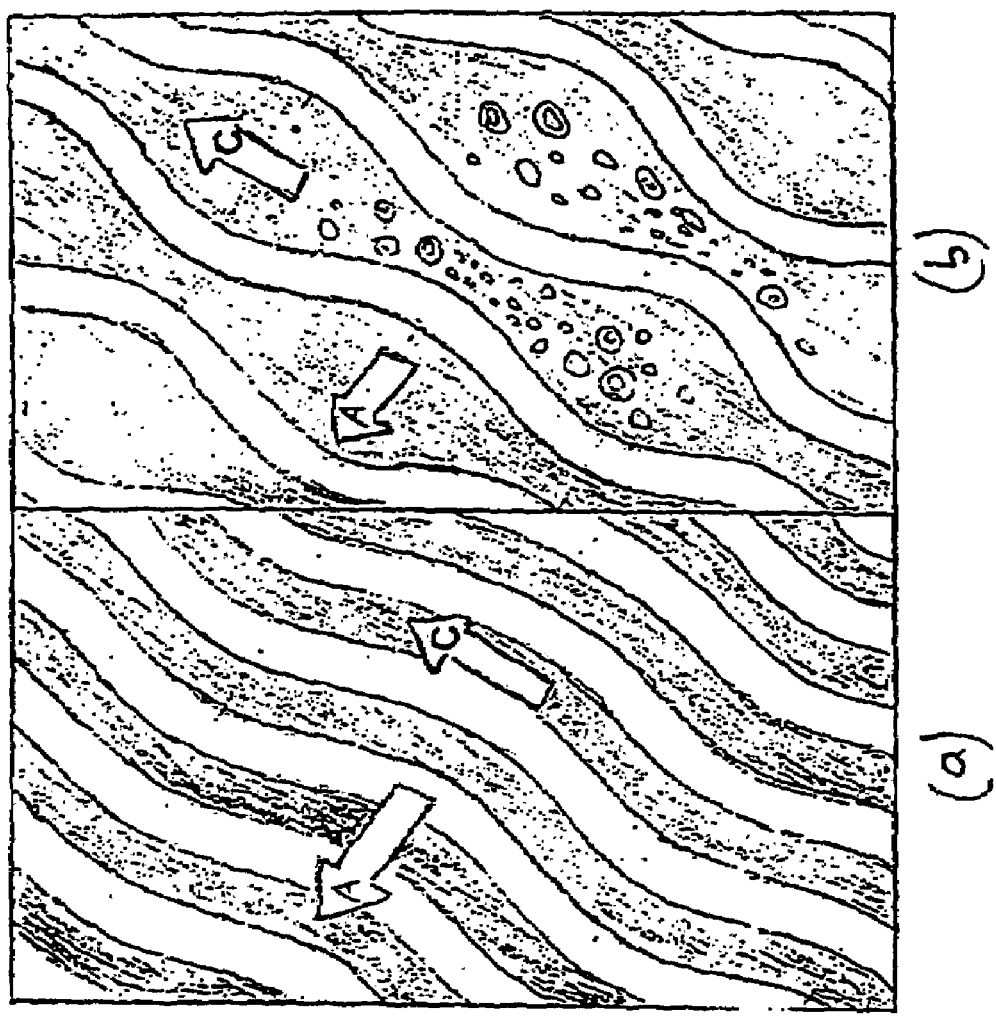
FIG. 6 shows curvilinear elements.

A variation of the stimulation image of FIG. 5 is shown in FIG. 6*a*. This image shows a plurality of parallel curvilinear stripes that move with the same linear and rotational movement characteristics as described for the straight edged stripe embodiment discussed above. However, a further movement with sinusoidal velocity is introduced in the direction of arrow C. FIG. 6*b* shows an image with non-parallel curvilinear stripes moving similar to the stripes in FIG. 6*a*. The non-parallel pattern produces 'globules' which travel in a direction transverse to the direction of the stripes. Non-cortical stimulation elements as described above can be placed in the regions between the stripes. These elements can be put into motion relative to the globules and made to behave in a varying manner, for example by accelerating the elements as they move through the narrow necks between the stripes.

Figure 7:
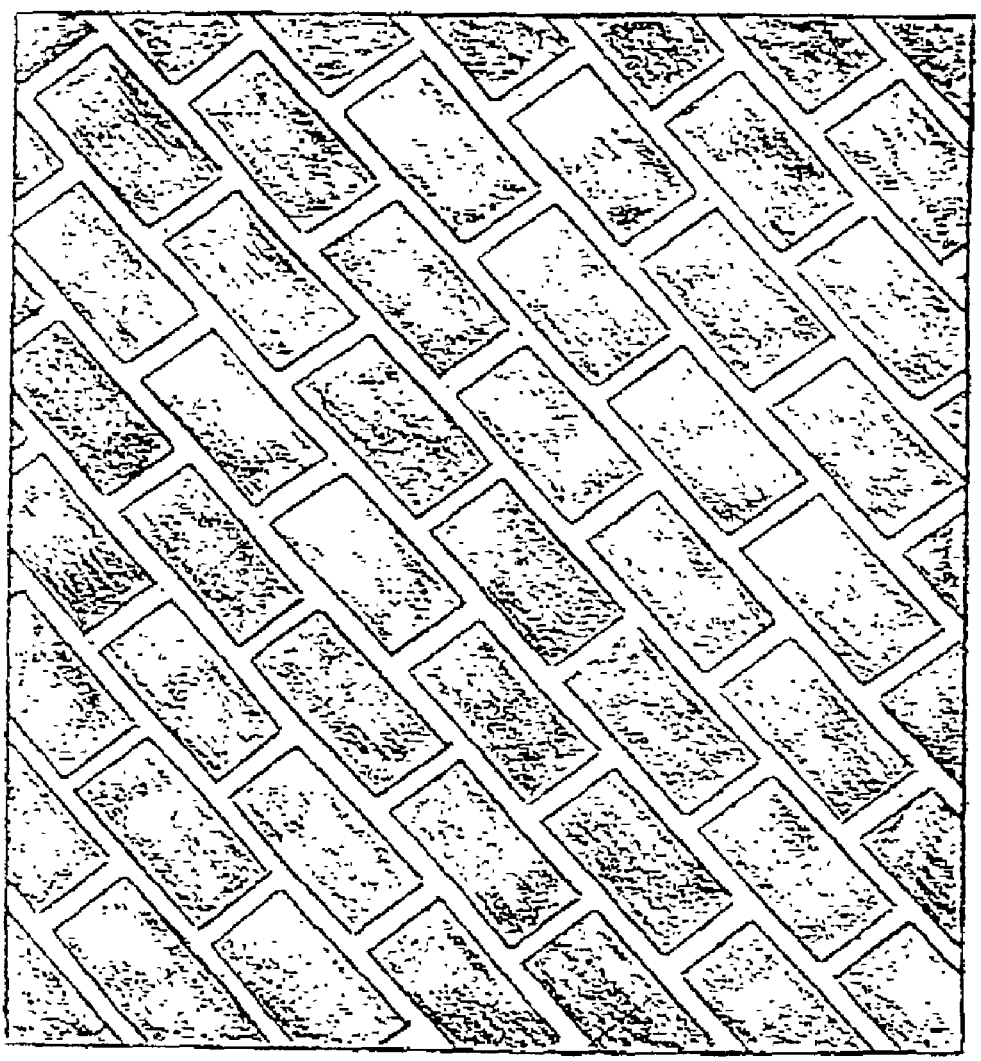
FIG. 7 shows a brick pattern of elements.

A further variation of the linear moving edge stimulation image is shown in FIG. 7. The image is presented as a brick wall pattern which includes movement characteristics as for the previously discussed images. The advantage of this image is that the provision of brick ends in a staggered configuration provides a further series of moving edges. An algorithm that is a part of the computer software takes account of image parameters chosen by the therapist during treatment. The length to width ratios and the orientation to direction ratios are progressively adjusted so that a patient can receive a full range of stimulations in a shorter time frame than is possible for the above described series of stripes. The variation of stimulation images as shown in FIG. 7 is particularly suitable for use with orientations moving in directions that are not transverse to the longitudinal direction of the bricks, as required by some cell fields, particularly in V5. The brick pattern may be used at an orientation angle approaching or equal to a horizontal direction of motion whilst still revealing an underlying cognitive exercise, which is not possible with the above described stripe patterns.

FIGS. 8 to 12 show a 'Diamond Multi-edge'" stimulation image designed to stimulate various portions of the visual cortex. The image was conceived as a means of providing the maximum number of moving edges of all dimensions, orientations, directions and velocities in a given time frame, for the maximal stimulation of the motion, velocity and orientation sensitive layers of the visual cortex and the extrastriate cortex. The image is formed from two overlying planes of stripes rotating relative to each other.

Figure 8:
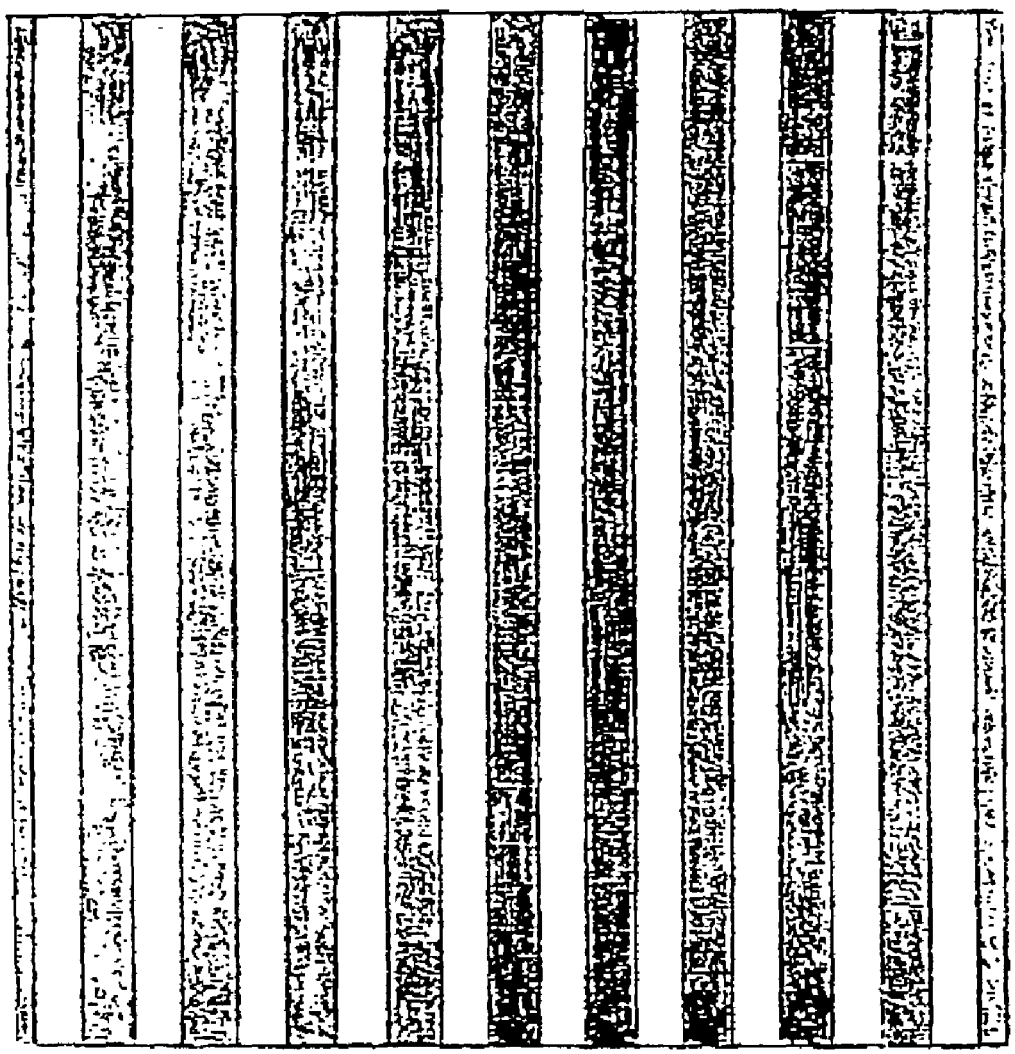
FIG. 8 shows two rotating planes of stripes in a first orientation.

FIG. 8 shows a 'snapshot' of when the two striped rotating fields are horizontal and exactly over one another. The stripe width and spacing is equal in this example. The stripe fields rotate in opposite directions about an axis at the centre of the monitor vision field and perpendicular to it. Both rotating fields are pan of a field which itself rotates.

Figure 9:
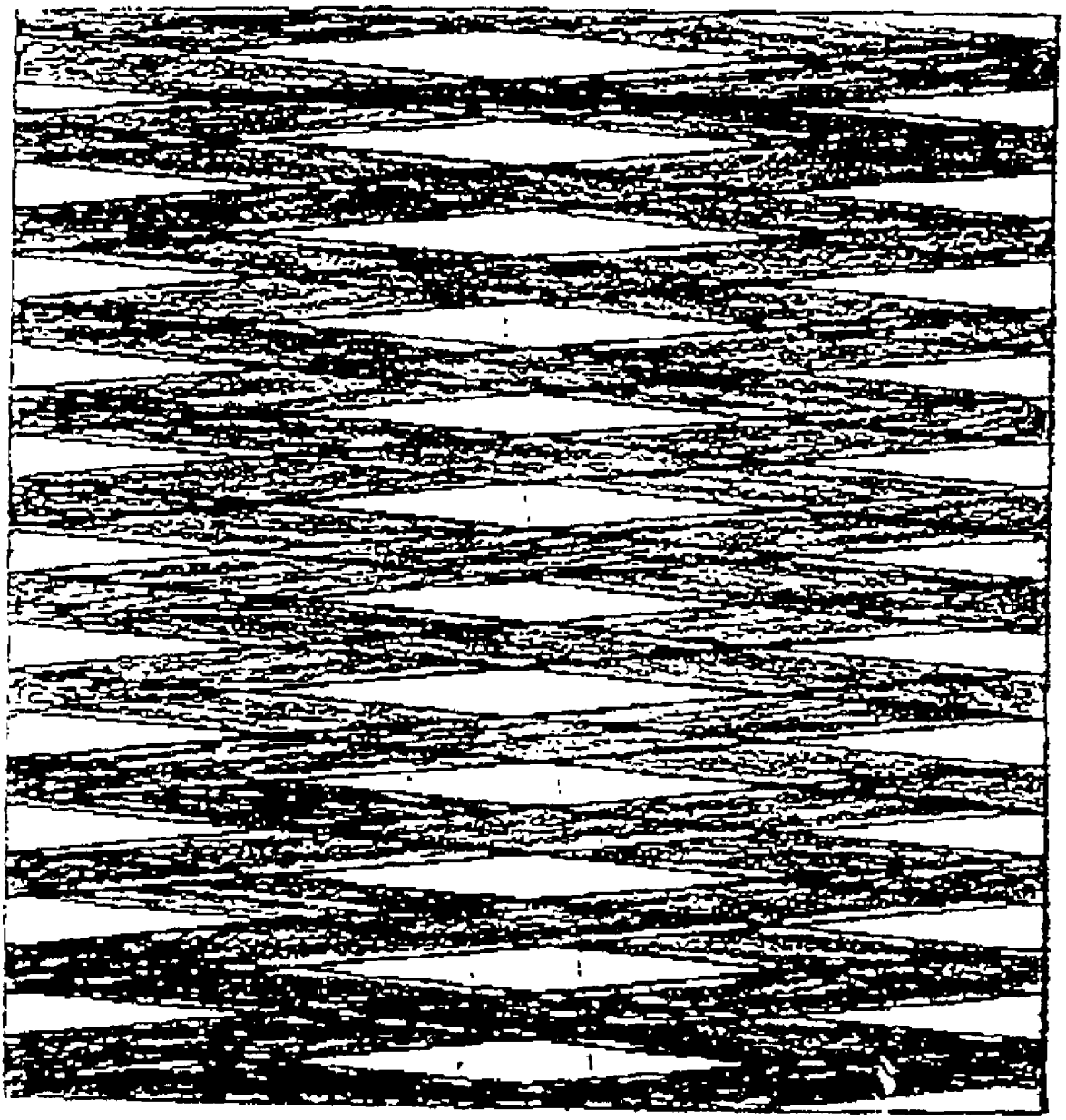
FIG. 9 shows the stripe planes of FIG. 8 in a second orientation.

FIG. 9 shows the display after striped planes have rotated just a few degrees. Diamond shapes appear that move towards the axis of the rotation.

Figure 10:
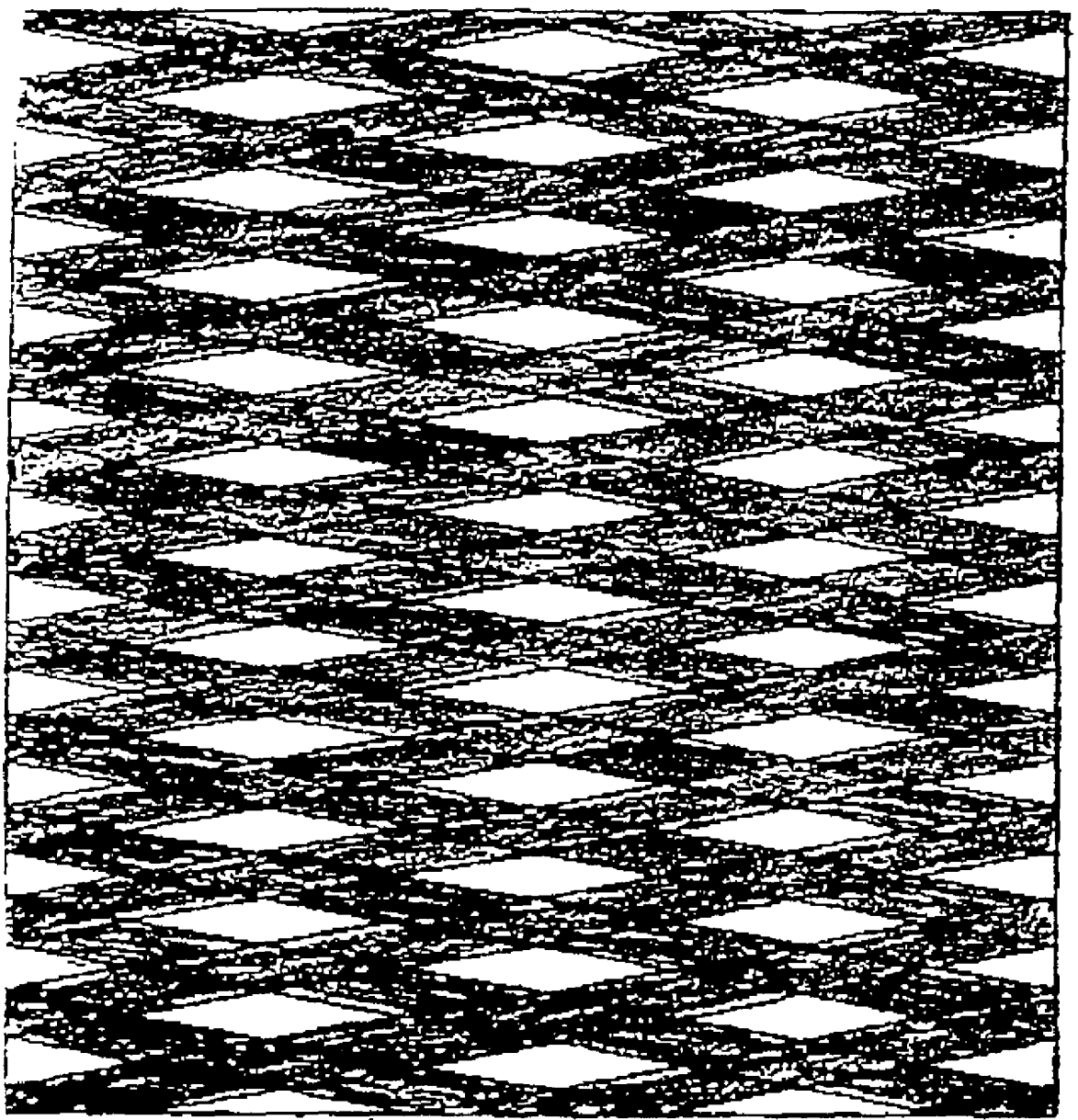
FIG. 10 shows the stripe planes in a third orientation.

FIG. 10 shows the display with further rotation than FIG. 9. The diamond shapes are more numerous and more 'squat'.

Figure 11:
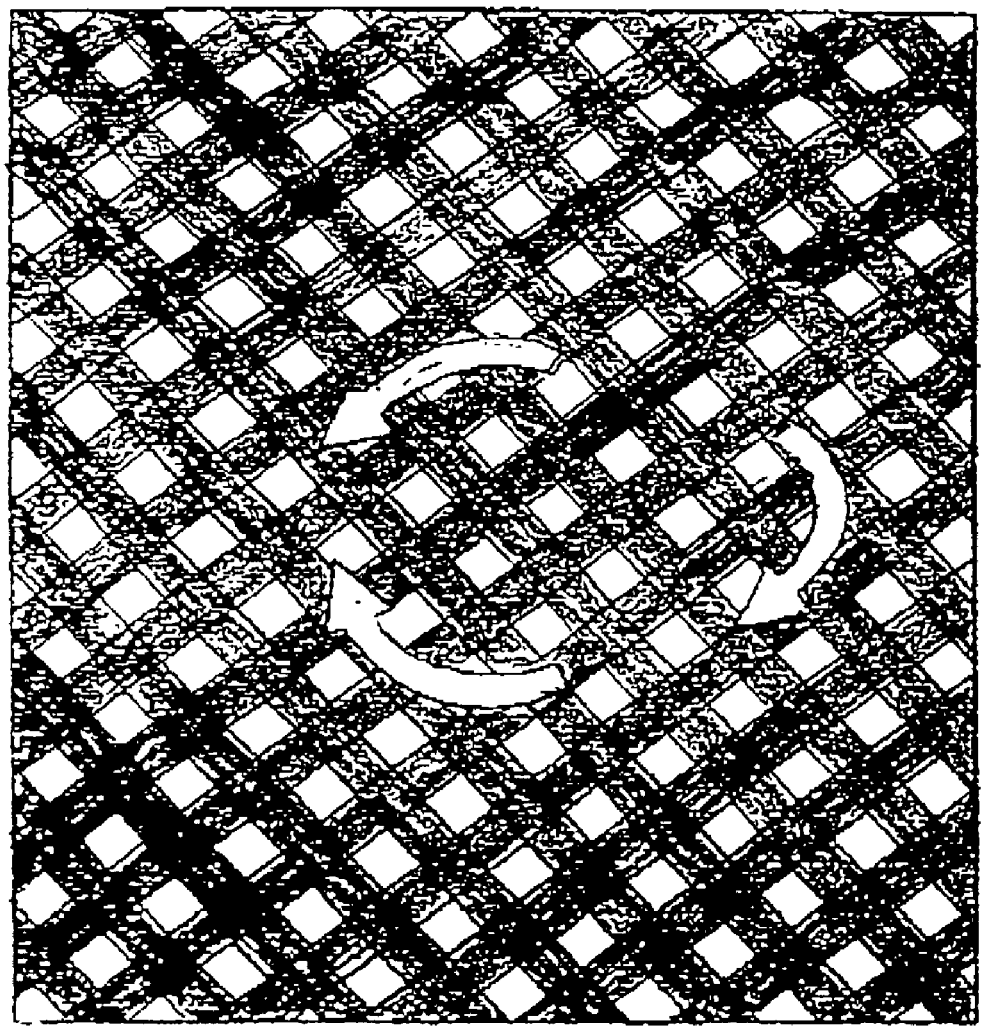
FIG. 11 shows the stripe planes in a fourth orientation.

FIG. 11 shows the display when the stripe planes are at 45 degrees. The diamond shapes are more numerous and with sides of equal length.

Figure 12:
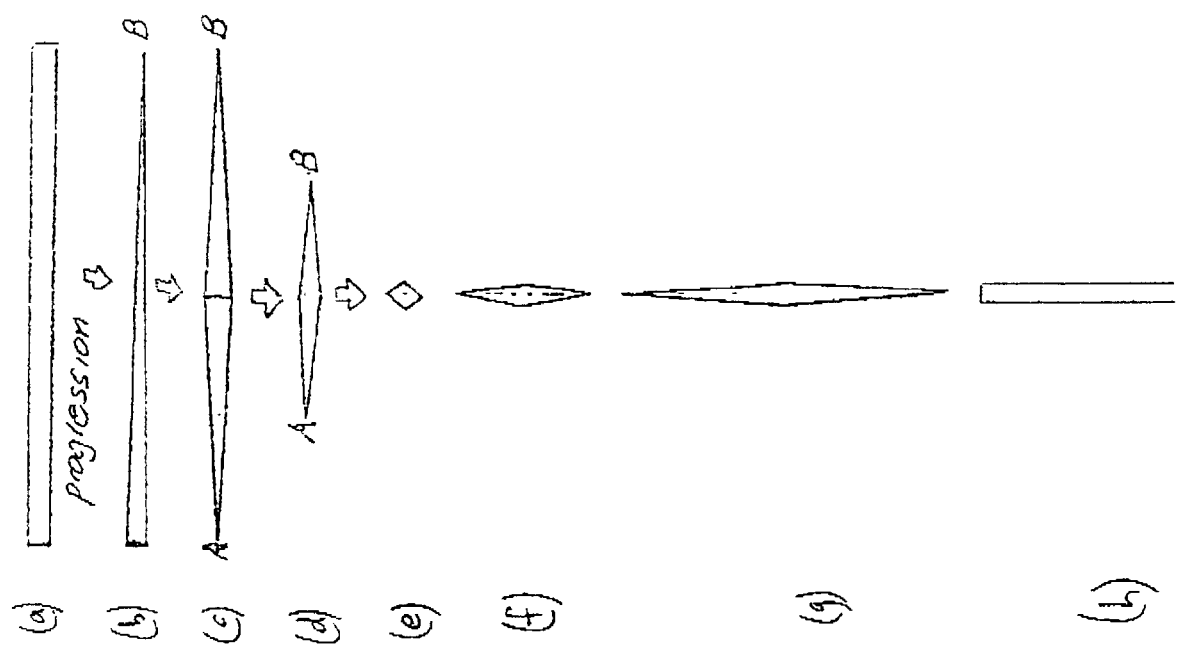
FIGS. 12(a) to 12(h) show the different images generated by the rotating stripe planes.

FIG. 12 shows a series of shapes created during the 'Diamond Multi-edge' stimulation image. The shapes shown are those created between a pair of stripes starting as in FIG. 8 (FIG. 12a). The rectangular shape rapidly becomes a diamond shape (FIG. 12c) which progressively becomes more compact (FIG. 12d), and is joined by other diamond shapes. The direction of motion of the diamonds relative to the reference plan is either a horizontal straight line, (starting as in FIG. 8) stationary at the 45 degree point as in FIG. 11 then switching to vertical motion. At the 90 degree rotation point, the display appears as in looks like FIG. 8 but vertical.

A slow rotation of the reference screen keeps altering the point at which FIG. 8 is seen. The computer software causes a background rotation of the entire reference plane so that the rectangles as in FIG. 8 are seen at every orientation within 360 degrees within a given treatment period.

It will be noted that the motion of the corners of the diamonds is substantially linear apart from the background rotation which causes a barely perceptible curve in the motion.

The present invention allows for the wavelength or colour of the stripes to be adjustable. With the appropriate selection of colour combinations, it is possible to create the visual conditions where the eye perceives the lines where the stripe of one plane crosses the other as 'edges'. This introduces a further large number of edges.

The rotational velocities of the stripes can be made non-linear and cyclic to ensure that every receptive cell field that is sensitive to particular velocities and orientations are stimulated within a treatment session in which the reference plane has rotated through 360 degrees. It is possible that parallel curvilinear stripes are used instead of rectangles so that more complex diamond shapes are generated.

As discussed previously, all cells can be stimulated with light or no light. It can be seen from a description of the cell types, that for a stimulation image to be effective, it needs to match the greatly varying characteristics of those cells. In the retino-geniculo portion of the pathway, the stimulation needs to be a mixture of dots, annuli and colours, with appropriate motion, timing, dimensions and contrasts. In the cortical portion of the pathway, there needs to be a stimulation regime with predominantly moving edges, bars, slits, shapes, with an appropriate motion, direction, velocity, dimensions, contrast as well as a dot regime as described above.

All of the characteristics of stimulation, need to be variable to accommodate the different dimensions, motions, velocities direction, time of exposure, colour requirements, contrast, luminance and viewing distance. No device in prior art has either the ability to provide the fine and varied adjustment required, or seeks to stimulate the receptive cell fields of the retino-geniculo-cortical pathway or beyond, as does the present invention.

When the stimulation regime based on cell characteristics is being used for treatment of the visual system, it will mostly be presented as a moving background to the interposed cognitive exertion regime, which is intended to be the focus of attention for the patient.

The interposed cognitive exertion regime is designed to ensure that the patient's eyes will be exposed to the background stimulation regime as a mixture of peripheral vision and direct vision. For this reason, the background stimulation could be thought as 'passive', in that it is capable of stimulating the cells without conscious effort on the part of the patient, in a similar way that electrical stimulation can contract and stimulate muscles. On the other hand, the interposed cognitive exertion regime is designed to force the concentration or the patient and think more deeply about the tasks that are presented.

Figure 13:
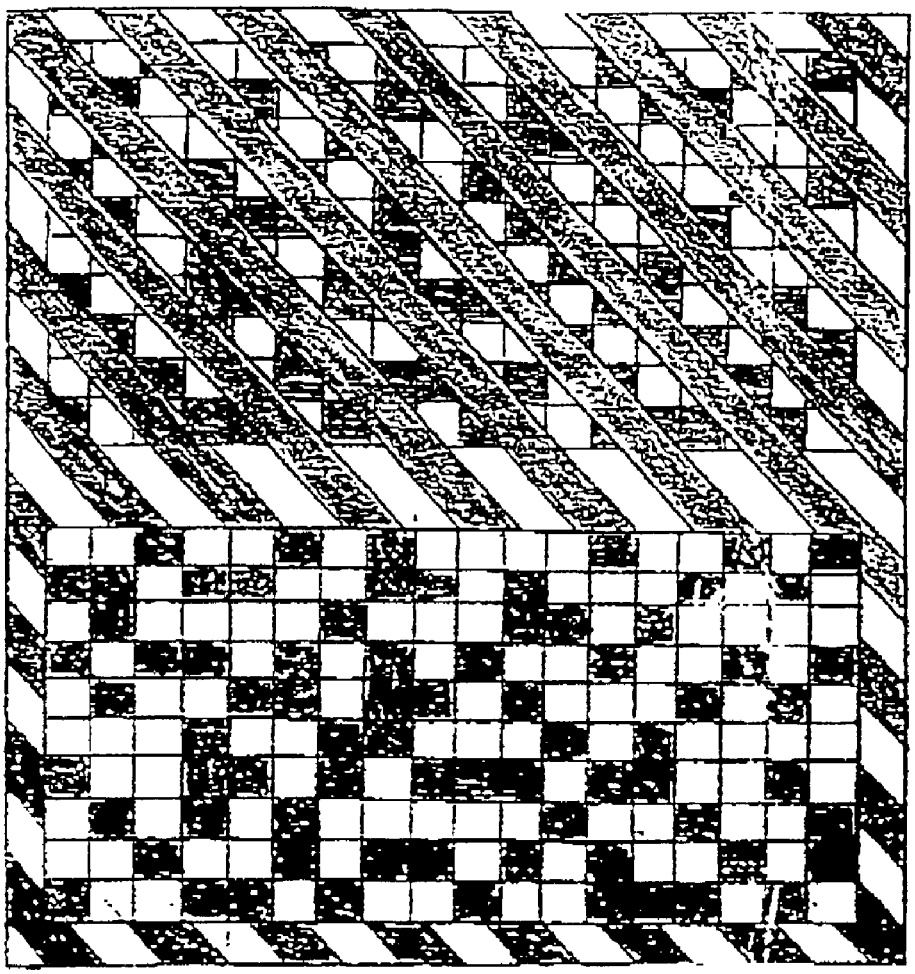
FIG. 13 is an example of a cognitive exertion exercise.

FIG. 13 shows an example of a stationary cognitive exertion exercise comprising a 'master board' of mosaics displayed on one half of the computer screen. A blank mirror image of the 'master board'—the 'target board'—is seen on the other half of the screen.

A passive background stimulation regime passes under the master board but over the target board. The stimulation image shown in this drawing is the linear omni-directional image.

The patient is required to 'click' on a dark mosaic on the master board to produce a copy, which then needs to be dragged to its mirror position on the target board. If the patient 'clicks' the correct position on the target board, the copy stays there. If not, the mosaic returns to its original place on the master board, registering an error.

A running score is kept to track the patient's performance. In this drawing, the time taken by the patient to fully complete the exercise is seen in digital form on the screen and is recorded. The objective of this treatment is for the patient to have a pass by the end of the last session at the degree of difficulty appropriate to the patient.

The degree of difficulty in this exercise can be adjusted in stages by the therapist or can be adjusted automatically by the computer software if the feedback from the patient indicates that an adjustment is necessary, either because the patient's performance is good, or the patient is having difficulty comprehending the exercise.

The blank target board can be made to move in a direction opposite to the moving stimulation background, constantly reappearing. Hence the patient is forced into greater visual effort by having a moving target and limited time.

A further stage of difficulty is achieved by reducing the contrast of the master and target boards. This places greater demands on the magnocellular pathways, which are debilitated in those patients with visually caused reading disorders.

This exercise is usually followed by a semantic version of it, where every square in the master and target boards is covered by coloured mosaics. The master board mosaics cover sentences or phrases. If the correct position on the target board is chosen, a letter is revealed on the corresponding position of the master board. If not, the mosaic returns to the master board without uncovering a letter. The objective is for the patient to be able to read the sentence or phrase with some letters covered. Every letter covered earns the patient points, which are accumulated.

This semantic version of this exercise helps enhance the patient's reading ability by improving short-term visual working memory and the patient's ability to construct whole words and phrase from fewer visual cues.

Both the passive and active stimulation regimes are specifically designed to expand working visual memory and enhance greater semantic recognition and recognition speed. This is achieved by fragmenting the visual and semantic tasks into moving elements and passing them underneath some of the opaque background stimulation elements. This is also achieved by passing the opaque background stimulation elements over stationary tasks or puzzles. The tasks are therefore seen periodically for short periods of time thus forcing the patient to remember shapes and portions of words long enough to be able to reconstruct them before they disappear from the screen. The complexity of the tasks and the time available for their completion can be progressively adjusted throughout the treatment to ensure that the patient is constantly improving.

Figure 14:
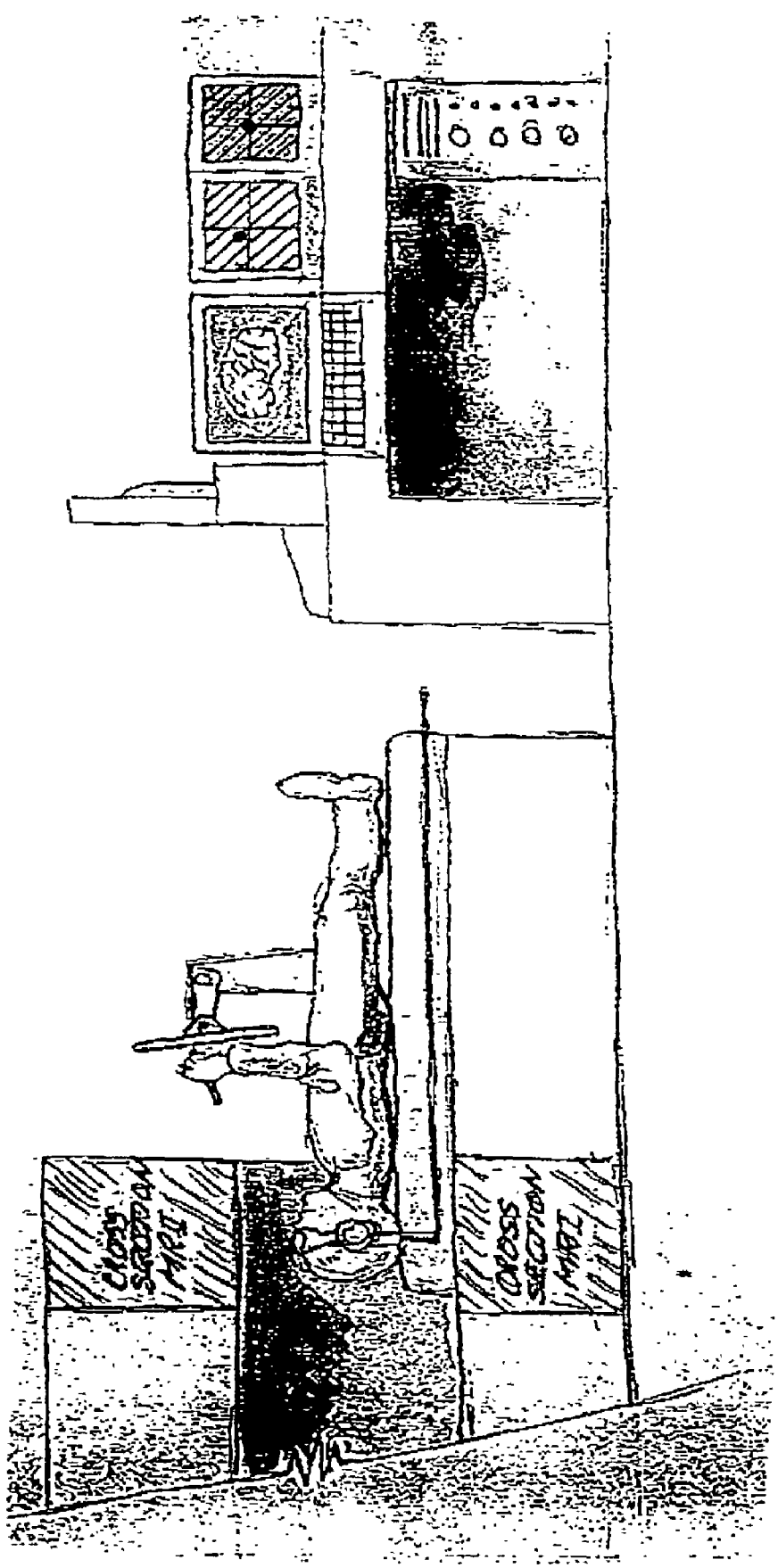
FIG. 14 shows an alternative embodiment of the present invention.

A further embodiment of the invention is described with reference to FIG. 14 in which a patient receives both visual and auditory stimulations. In the embodiment shown, the patient visual display unit is a pair of virtual reality goggles connected to the computer processor to receive the display images. The patient also wears a set of headphones for receiving auditory signals. The goggles and headphones may be integrated into one piece of headwear such as a helmet. The apparatus shown may further include microphones and recording devices for receiving spoken responses from the patient, and speech recognition software in the computer processor for suitably processing the patient's speech.

Those diagnosed with auditory and phonological impairments will be presented with aural tasks consisting of sounds and speech. These aural tasks will relate to visual elements on the monitor that will be partially seen between a visual stimulation background that is chosen and adjusted to suit the patient. The patient response will be a mixture of the spoken, the written, the drawn and the visual. Working memory enhancement will therefore be simultaneously auditory and visual.

Figure 15:
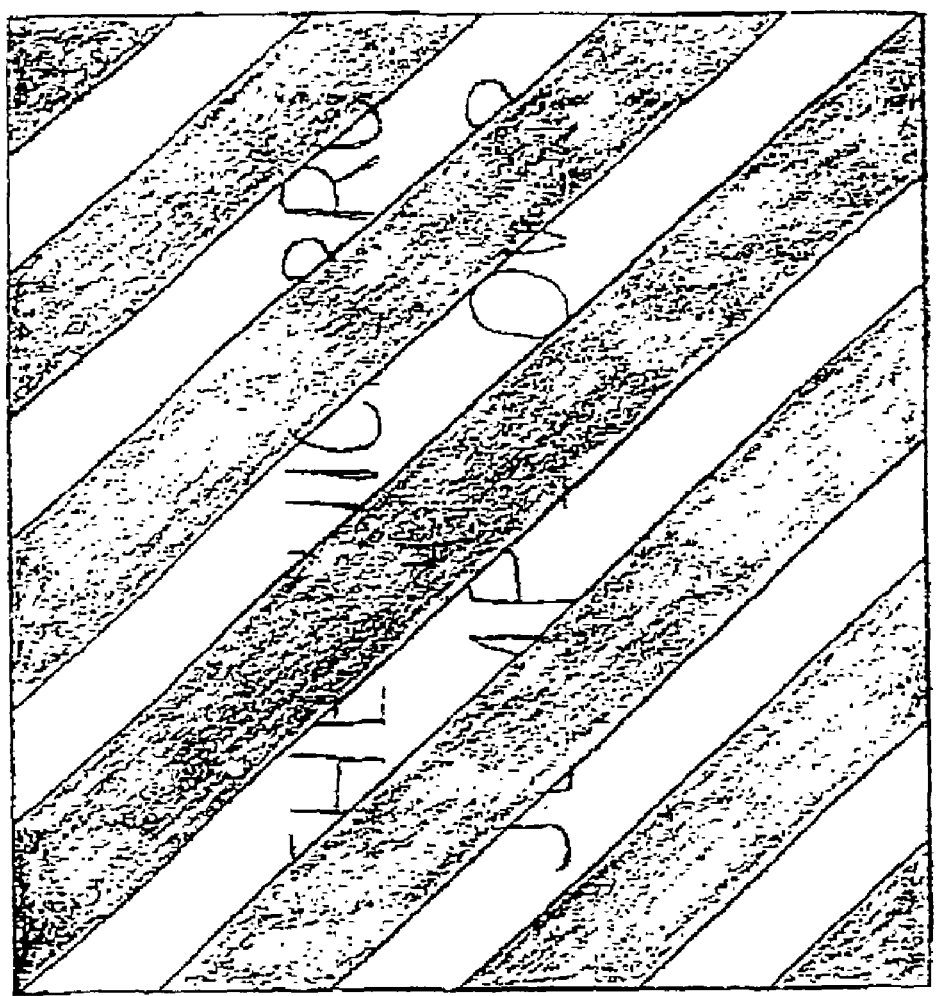
FIG. 15 shows a cognitive exertion exercise incorporating an auditory component.

The aural task may be a simple task as shown in FIG. 15 where text is initially presented to the patient aurally before it is displayed on the screen. The patient will need to correctly interpret the combination of phonemes making up the originally presented words and make a correct auditory semantic recognition of the words, phrase or sentence. This recognition needs to reside in the patient's auditory working memory. The text will then appear in visual form and move underneath the passive stimulation elements. The patient will need to make semantic visual recognition from the bits and pieces of words passing between the spaces of the background, and put them together in a phrase or sentence before they disappear off screen.

A further example of a combined aural/visual cognitive exertion exercise is described with reference to FIG. 16. In this figure, a series of auditory exertion exercises are shown.

A cognitive exercise is presented aurally to the patient when there is nothing on the screen except an active linear omni-directional visual stimulation regime, adjusted for a patient with a 'phonological bias'. Only after the aural input has been made, the visual cognitive exercise corresponding to that input appears, requiring the patient to remember what has been said and to respond accordingly.

The exercises given are selected from an archive that is categorised by gender, race, and cultural background. Language is modified to be regionally appropriate with respect to idiom and accent. Exercises involve phonemes of difficulty particular to the patient can be selected.

Responses are to be made by the patient who is able to look at the screen and indicate a response by pointing to an object using a stylus held as a writing instrument on an electronic work tablet. Objects are dragged in accordance to the aural instructions, without the patient having to take his or her eyes off the computer screen. For example, for the exercise depicted in FIG. 16, an auditory input is provided to the patient in the form:—

"Benjamin is a happy boy"

"Harold is unhappy"

"Match the name with the face by dragging a name over the face"

The image in FIG. 16 then appears on the screen and the patient has to perform the spoken task.

Incorrect responses, if dragged to the correct subject, will return by themselves to their pre-programmed path, with an error recorded by the system against the patient. An incorrect response dragged to an incorrect subject will be recorded as two errors.

A database of the computer processor will keep a record of the patient's responses to treatment as a means of assessing rates and degrees of patient improvement.

For each of these exercises involving a speech input the speech will be presented with the spectral content of normal speech but with an electronically modified temporal content to provide more time for the patient to recognise the different phonemes they are unable to recognise in unmodified speech. The temporal component can then be adjusted as the patient improves to increase the speed of the speech inputs without modifying their sound.

It is of particular importance for those with reading disorders to acquire a healthy stereopsis through sound binocular vision. Fixation problems at an early age can lead to one eye dominance and to the debilitation of the other eye. This would include the debilitated eye's magnocellular pathways, the debilitation of which could cause vision timing problems as previously discussed. There can also be a diminished ability to perform microsaccades and to control fixation slip that could lead to less accurate symbol identification and semantic recognition problems.

An important element in the treatment of reading disorders according to the present invention is the restoration and maintenance of binocularity throughout the treatment. This can be achieved through normal orthoptic procedures that involve initial occlusion following by a coloured lens filtering of the dominant eye as is known from prior art treatments of ocular fixation disorders. However, the present invention is well suited to make use of new display technologies such as virtual reality goggles and direct retinal imaging to provide varying levels of occlusion. In particular, these technologies can be used to display the same image to each eye with modifications to be viewed by one eye only, or alternatively a separate image can be displayed to each eye.

Figure 17:
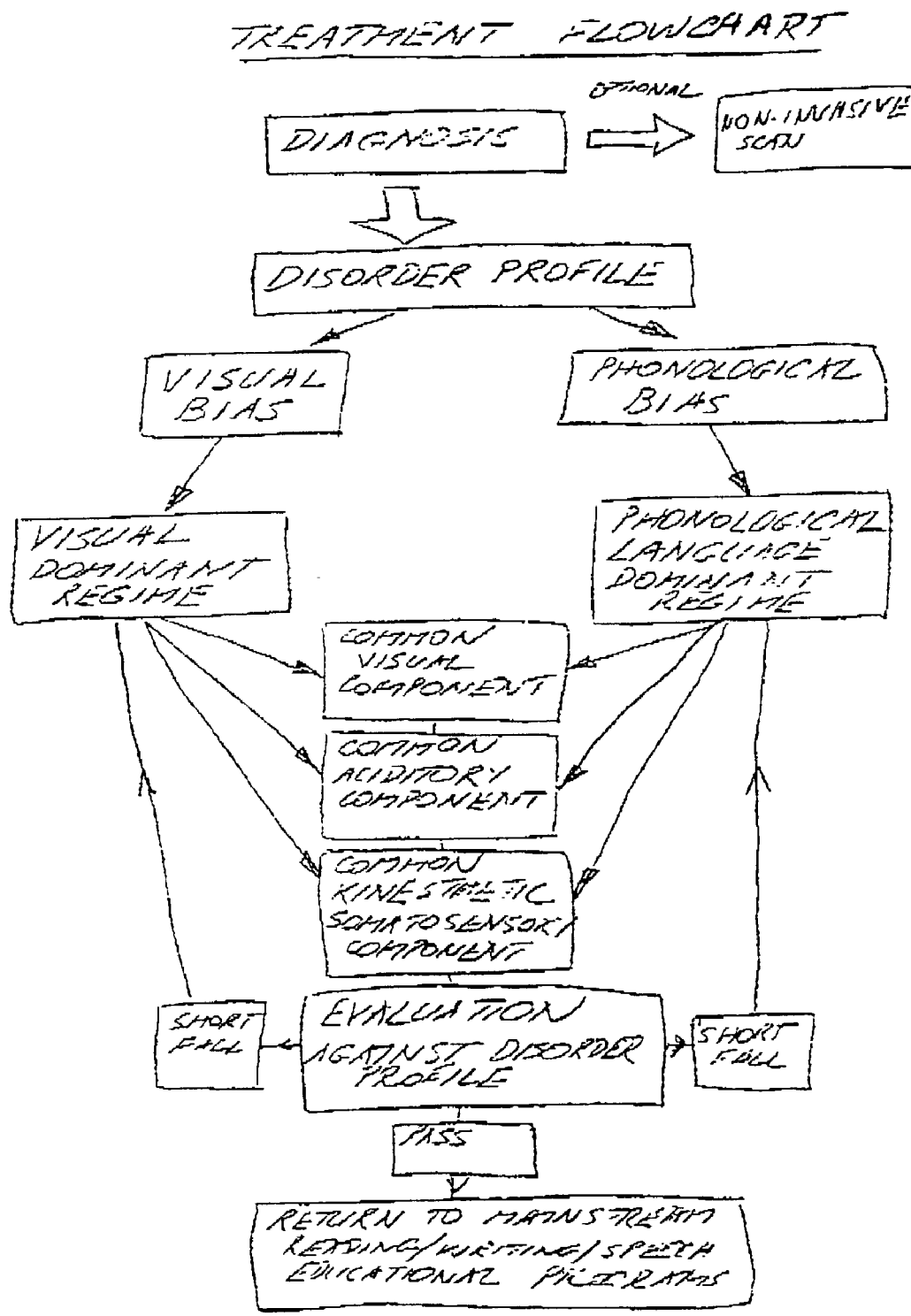
FIG. 17 shows a flow chart for treatment according to the invention.

FIG. 17 shows a treatment flow chart in accordance with the invention. The first stage of a patient's treatment is diagnosis by conventional means to determine the debilitation profile of the patient and in particular whether the patient's disorders are predominantly visually caused or phonologically caused. After diagnosis, the patient's treatment can proceed down either the visual or phonological treatment streams depending on the diagnosis.

The visual stream is more visually biased. Adequate semantic recognition abilities are essential for normal reading. Hence the auditory input regime will be the supplementary to the visual treatment. These will require oral, visual or kinaesthetic responses (writing or drawing). For the visual stream, the auditory inputs will not have their temporal characteristics modified digitally as is required for those that are phonologically impaired. The oral or kinaesthetic inputs will be intensified if the disorder profile indicates the need.

The phonological stream is more phonologically biased. Adequate oculomotor and stereopsis is essential for normal reading. Hence a visual treatment regime is supplementary to the phonological treatment regime, incorporating less visually intensive parameters.

The connection between writing and visual or auditory memory is well known. Throughout treatment according to this invention, whether it be by the visually or phonologically biased treatment streams, the patient is required to write or draw words and phrases, by means of the stylus and work pad. The degree to which the treatment requires writing is determined by the patient's initial debilitation profile.

A large area of the brain is allotted to the sense of touch, with numerous interconnections that include the visual and auditory systems. Although all the functional consequences of somatosensory debilitations on the visual and auditory systems are not known to the inventor, abnormally slow speed threshold differences in somatosensory functions can be found when patients also exhibit slow speed threshold processing abnormalities in either the visual or auditory processing areas.

Part of the debilitation profile that is prepared according to the present invention, will include a somatosensory threshold speed assessment. Should the profile warrant it, a segment of the treatment will be dedicated to a somatosensory stimulation regime via a regulated threshold speed monitoring device that will be integrated with a visual stimulation regime, as well as with visual and auditory cognitive tasks.

An inventive aspect of the present invention is that it can provide linearly moving stimulation elements. This is important as many neurophysiological processes such as reading have an inherently linear nature due to the usual display of text.

The present invention is well suited to make use of existing developments in non-invasive techniques for measuring brain activity such as functional Magnetic Resonance Imaging (fMRI) and Positron Emission Tomography (PET). During a patient's treatment different brain responses can be monitored and provided to the computer processor. The computer processor may then track which stimulation images and cognitive exertion exercises generate the highest levels of brain activity and ensure that these images and exercises are enhanced during a patient's treatment. This aspect of the invention can therefore assist in developing a specific treatment profile for a particular patient to optimise the patient's treatment. The optimisation may be performed automatically by the software that controls the display acting on feedback from the brain monitoring, or by the therapist. Brain activity monitoring can also be used to develop new stimulation images and cognitive exertion exercises that will be of benefit to the patient. The apparatus required for brain activity monitoring can be incorporated into the headwear used for providing the display to the patient as described previously with reference to FIG. 14.

The above described treatment methods apart from being able to treat reading disorders such as dyslexia, and writing and speech disorders, also has application in the treatment of Attention Deficit Hyperactivity Disorder (ADHD). Research has shown that people suffering ADHD have similar neurophysiological debilitations as described for the present invention. Therefore the multi-sensory treatments described according to the present invention are capable of rehabilitating ADHD sufferers. Hence the present invention offers the possibility of a longer term cure for ADHD without the social and medical problems that a drug based treatment can cause.

A further application of the present invention is in the enhancement of the neurophysiological process, in particular movement perception, in people who do not suffer from a visual disorder. Such people may for example be sportspeople looking to enhance their sporting abilities or defence personnel where good visual perception may at times be a necessary survival skill. For these treatments specific stimulation images and cognitive exertion exercises may be generated. For example, the treatment may make use of existing virtual reality technology to create a cognitive exertion exercise where a sportsperson is presented with a realistic sporting situation such as a baseball batter receiving a pitch. The apparatus may also include as part of the virtual display a baseball bat that the patient wields to receive the pitch, the exercise being to make properly timed contact with the virtual ball. The virtual reality display would also include moving stimulation display elements as discussed above for the passive enhancement of the receptive cell fields of the patient's visual pathways.

In a defence context, the virtual stimulation images may use specific colours that enhance a person's ability to perceive movement in a camouflage environment.

Further application of the present invention will be apparent to the skilled reader.

While particular embodiments of this invention have been described, it will be evident to those skilled in the art that the present invention may be embodied in other specific forms without departing from the essential characteristics thereof. The present embodiments and examples are therefore to be considered in all respects as illustrative and not restrictive, the scope of the invention being indicated by the appended claims rather than the foregoing description, and all changes which come within the meaning and range of equivalency of the claims are therefore intended to be embraced therein.

The invention claimed is:

1. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said first visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise;

further including second visual display means to be viewed by a therapist and therapist input means allowing said therapist to provide inputs to said processing means to vary said display;

further including feedback means providing an indication of said patient's performance to said computer processing means, and means for indicating said performance on said second visual display means; and further including means for varying the display on said first visual display means to optimise said patient's brain response.

2. Apparatus according to claim 1 wherein the variations to the display on said first visual display means are made by said computer processing means without input from said therapist.

3. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said first visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise; and further including means for controlling said patient's position relative to said first visual display means, wherein said means for controlling said patient's position includes an electronically controllable seat capable of moving up, down and laterally, an electronically controllable backrest and an electronically controllable headrest.

4. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said first visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise, wherein said visual stimulation image includes a plurality of dots and annuli.

5. Apparatus according to claim 4 wherein said visual stimulation image includes a dot surrounded by a contrasting annulus.

6. Apparatus according to claim 4 or 5 wherein said visual stimulation image provides stimulation to concentrically organised receptive cell fields of a patient.

7. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said first visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise, wherein said therapeutic display elements include a first plane of parallel stripes rotating relative to a second plane of parallel stripes.

8. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said first visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise, wherein said therapeutic display elements include a brick pattern.

9. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said first visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise, wherein at least one of said therapeutic display elements moves to at least partially obscure a displayed cognitive exertion exercise.

10. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more contrast edges moving in a substantially linear path, wherein said therapeutic display elements are displayed on said visual display means so as to provide therapeutic stimulation to said receptive cell fields of a patient whilst said patient is performing said cognitive exertion exercise, wherein said therapeutic display elements include a dot surrounded by a contrasting annulus.

11. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more contrast edges moving in a substantially linear path, wherein said therapeutic display elements are displayed on said visual display means so as to provide therapeutic stimulation to said receptive cell fields of a patient whilst said patient is performing said cognitive exertion exercise, wherein said therapeutic display elements are a pattern of bricks.

12. Apparatus according to claims 10 or 11 wherein the locus of movement of said visual display elements is periodically adjusted.

13. Apparatus for the enhancement of neurophysiological processes of a patient by the stimulation of receptive cell fields in the visual pathways of the patient between the retina and the visual cortex, the apparatus including first visual display means for viewing by said patient and computer processing means producing an output to said visual display means to cause a display on said visual display means, said display including at least one visual cognitive exertion exercise and at least one visual stimulation image including one or more therapeutic display elements targeted to stimulate selected ones of said receptive cell fields, said therapeutic display elements including one or more moving contrast edges, wherein said therapeutic display elements are displayed on said visual display means so as to provide therapeutic stimulation to said receptive cell fields of a patient whilst said patient is performing said cognitive exertion exercise, said apparatus further including means for generating an auditory cognitive exertion exercise including one or more auditory signals related to at least one of said visual cognitive exertion exercises, wherein said auditory cognitive exertion exercise is related to a visual cognitive exertion exercise displayed on said first visual display means and requires said patient to focus on said related visual cognitive exercise, wherein said auditory signals are computer generated speech signals, and wherein said speech signals are acoustically modified by said computer processing means such that the temporal portion of said speech is adjusted but the spectral portion of said speech remains substantially constant.

14. Apparatus according to claim 13 wherein said auditory signals are modified in response to input from a therapist.

15. A method of enhancing neurophysiological processes of a patient by the stimulation of receptive cell fields in the visual pathways of the patient between the retina and the visual cortex, the method including the steps of generating an output from computer processing means to cause a display on visual display means for viewing by said patient, said display including at least one visual cognitive exertion exercise and at least one visual stimulation image including one or more therapeutic display elements targeted to stimulate selected ones of said receptive cell fields, said therapeutic display elements including one or more moving contrast edges, wherein said visual stimulation image provides therapeutic stimulation to selected ones of said receptive cell fields whilst said patient is performing said visual cognitive exertion exercise, the method further including the step of receiving at said computer processing means feedback representing said patient's brain activity.

16. A method according to claim 15 further including the step of varying said display to optimize said patient's brain activity.

17. A method of enhancing neurophysiological processes of a patient by the stimulation of receptive cell fields in the visual pathways of the patient between the retina and the visual cortex, the method including the steps of generating an output from computer processing means to cause a display on visual display means for viewing by said patient, said display including at least one visual cognitive exertion exercise and at least one visual stimulation image including one or more therapeutic display elements targeted to stimulate selected ones of said receptive cell fields, said therapeutic display elements including one or more moving contrast edges, wherein said visual stimulation image provides therapeutic stimulation to selected ones of said receptive cell fields whilst said patient is performing said visual cognitive exertion exercise, wherein said visual stimulation image includes a plurality of dots and annuli.

18. A method according to claim 17 wherein said visual stimulation image includes a dot surrounded by a contrasting annulus.

19. A method according to claim 17 or 18 wherein said visual stimulation image provides stimulation to concentrically organized receptive cell fields of a patient.

20. A method of enhancing neurophysiological processes of a patient by the stimulation of receptive cell fields in the visual pathways of the patient between the retina and the visual cortex, the method including the steps of generating an output from computer processing means to cause a display on visual display means for viewing by said patient, said display including at least one visual cognitive exertion exercise and at least one visual stimulation image including one or more therapeutic display elements targeted to stimulate selected ones of said receptive cell fields, said therapeutic display elements including one or more moving contrast edges, wherein said visual stimulation image provides therapeutic stimulation to selected ones of said receptive cell fields whilst said patient is performing said visual cognitive exertion exercise, wherein said therapeutic display elements include a first plane of parallel stripes rotating relative to a second plane of parallel stripes.

21. A method of enhancing neurophysiological processes of a patient by the stimulation of receptive cell fields in the visual pathways of the patient between the retina and the visual cortex, the method including the steps of generating an output from computer processing means to cause a display on visual display means for viewing by said patient, said display including at least one visual cognitive exertion exercise and at least one visual stimulation image including one or more therapeutic display elements targeted to stimulate selected ones of said receptive cell fields, said therapeutic display elements including one or more moving contrast edges, wherein said visual stimulation image provides therapeutic stimulation to selected ones of said receptive cell fields whilst said patient is performing said visual cognitive exertion exercise, wherein said therapeutic display elements include a brick pattern.

22. A method of enhancing neurophysiological processes of a patient by the stimulation of receptive cell fields in the visual pathways of the patient between the retina and the visual cortex, the method including the steps of generating an output from computer processing means to cause a display on visual display means for viewing by said patient, said display including at least one visual cognitive exertion exercise and at least one visual stimulation image including one or more therapeutic display elements targeted to stimulate selected ones of said receptive cell fields, said therapeutic display elements including one or more moving contrast edges, wherein said visual stimulation image provides therapeutic stimulation to selected ones of said receptive cell fields whilst said patient is performing said visual cognitive exertion exercise, wherein at least one of said therapeutic display elements moves to at least partially obscure a displayed cognitive exertion exercise.

* * * * *